United States Patent [19]

Kowanko

[11] Patent Number: 5,385,606
[45] Date of Patent: Jan. 31, 1995

[54] ADHESIVE COMPOSITION AND METHOD

[76] Inventor: Nicholas Kowanko, 618 S. Fifth St., Moorhead, Minn. 56560

[21] Appl. No.: 34,184

[22] Filed: Mar. 22, 1993

Related U.S. Application Data

[63] Continuation of Ser. No. 908,474, Jul. 6, 1992, abandoned.

[51] Int. Cl.⁶ .......................... C08L 89/00; C08H 1/02
[52] U.S. Cl. .................... 106/124; 106/125; 527/205
[58] Field of Search ............... 106/125, 124; 527/205; 530/829, 830, 380; 524/17, 18, 9, 10, 354, 541; 602/50, 904; 604/307; 606/154, 153; 424/443, 444, 43; 514/2

[56] References Cited

U.S. PATENT DOCUMENTS

| | | | |
|---|---|---|---|
| 2,241,868 | 5/1941 | Reimann | 530/382 |
| 2,492,458 | 12/1949 | Bering, Jr. | 424/443 |
| 2,597,228 | 5/1952 | Cornwell | 530/380 |
| 3,395,106 | 7/1968 | Curtis | 527/205 |
| 4,362,567 | 12/1982 | Schwartz | 106/157 |
| 4,414,976 | 11/1983 | Schwarz et al. | 106/161 |
| 4,427,650 | 1/1984 | Stroetmann | 424/46 |
| 4,427,651 | 1/1984 | Stroetmann | 424/46 |
| 4,626,310 | 12/1986 | Riter | 156/307.3 |
| 4,627,879 | 12/1986 | Rose | 106/124 |
| 4,650,678 | 3/1987 | Fuhge | 424/101 |
| 4,740,534 | 4/1988 | Takehisa | 523/118 |
| 4,813,958 | 3/1989 | Dixon | 623/11 |
| 4,816,251 | 3/1989 | Seelich | 424/101 |
| 4,818,291 | 4/1989 | Iwatsuki | 106/124 |
| 4,983,392 | 1/1991 | Robinson | 424/427 |
| 5,099,003 | 3/1992 | Kotitschke et al. | 530/382 |

FOREIGN PATENT DOCUMENTS

| | | |
|---|---|---|
| 251126 | 9/1912 | Germany . |
| 3230849A1 | 2/1989 | Germany . |
| 57-149229 | 9/1982 | Japan . |
| 741878 | 6/1990 | U.S.S.R. . |

OTHER PUBLICATIONS

Braunwald et al. "Evaluation of crosslinked gelatin as a tissue adhesive and lenstatic agent: An experimental study". Surgery—Jun 1966, pp. 1024–1030.

Rose "Gelatin" Encyclopedia of Polymer Science and Engineering, pp. 488≧513, 1987 (month unavailable).

Encyclopedia of Polymer Science and Engineering, vol. 1, pp. 547–577, USA, John Wiley and Sons 1985, "Adhesive Compositions" Temin et al. (month of publication unavailable).

Brothers, M. F., Kaufmann, J. C., Fox, A. J., Deveikis, J. P.: "n-Butyl 2-cyanoacrylate–substitute for IBCA in interventional neuroradiology: histopathologic and polymerization time studies." *Ajnr–American Journal of Neuroradiology* 10(4) (Jul.–Aug. 1989), Abstract.

Jebara, V. A., Fabiani, J. N., Couetil, J. P., Acar, C., Dreyfus, G. Delouche, A., Carpentier, A.: "Exclusive use of surgical glue without graft replacement for type A aortic dissection: A new technique." *European Heart Journal* (1989)

Beloglazova, S. E.: "Cyanoacrylate glues and their use in gynecology [Rus]". *Akusherstvo I Ginekologiia—Moskva* (5) (May 1988), Abstract.

Byrne, D. J., Hardy, J., Wood, R. A., McIntosh, R., Cuschieri, A.: "Effect of fibrin glues on the mechanical properties of healing wounds." *British Journal of Surgery* 78(7) (Jul. 1991), Abstract.

Laitakari, K., Luotonen, J.: "Autologous and homologous fibrinogen sealants: adhesive strength." *Laryngoscope* 99(9) (Sep. 1989), pp. 974–976.

Beltramello, A., Benati, A., Perini, S., Maschio, A.: "Interventional angiography in neuropediatrics." *Childs Nervous System* 5(2) (Apr. 1989), Abstract.

Gigauri, V. S., Movchun, A. A., Got'e, S. V., Sheremet'eva, G. F., Shidkov, I. L.: "Use of fibrin glue in (List continued on next page.)

*Primary Examiner*—John Kight, III
*Assistant Examiner*—Jeffrey Culpeper Mullis
*Attorney, Agent, or Firm*—Fredrikson & Byron

[57] ABSTRACT

An adhesive composition, primarily intended as a tissue adhesive, comprised of cross-linked proteinaceous material, and methods for its use.

19 Claims, No Drawings

OTHER PUBLICATIONS surgery of parenchymatous organs [Rus]." *Khirurglia* (4) (Apr. 1989), Abstract.

Sackett, D. L.: "Simple and inexpensive preparation of dried polyacrylamide gels for densitometry and/or storage." *Analytical Biochemistry* 179(2) (Jun. 1989), Abstract.

"Dura mater healing after repair with aponeurotic plasty. Comparison of results between classical sutures and fibrin adhesive glue. Fibrin adhesive in frontobasal injuries. An experimental study [Fre]." Neuro-Chirurgie 34(5) (1988), pp. 1024–1030.

Havlicek, K., Vlcek, B., Stastny, J.: "Hemostatic and adhesive properties of fibrin tissue glue in an experiment." *Rozhldey V Chirugii* 70(5) (Mar. 1991), Abstract.

Herter, T.: "Is there a preference among fibrin glues for nerve anastomosis? [Ger]."Hno. 37(6) (Jun. 1989), Abstract.

Siedentop, Karl H., Harris, David M. Sanchez, Ben: "Autologous Fibrin Tissue Adhesive: Factors Influencing Bonding Power" Laryngoscope 98 Jul. 1988.

Aprahamian, Marc, Lambert, Alain, Balboni, Ginette, Lefebvre, Francoise, Schmitthaeusler, Roland, Damge, Cristiane, Rabaud, Michel: "A new reconstituted connective tissue matrix: Preparation, biochemical, structural and mechanical studies." *Journal of biomedical Materials Research* vol. 21 (1987), pp. 965–977.

Meyer, G., Muster, D., Schmitt, D., Jung. P., Jaeger, J. H.: "Bone Bonding Through Bioadhesives: Present Status." *Biomat., Med. Dev., Art. Org.* 7(1) (1979).

Tom Majeski, St. Paul Pioneer Press Jun. 15, 1992. Researchers Stick To The Job, Create A Surgical Glue.

Marescaux, J. F., Aparahamian, M., Mutter, D., Loza, E., Wilhelm, M., Sonzini, P., Damge, C.: "Prevention of anastomosis leakage: an artificial connective tissue." *Br. J. Surg.* vol. 78, No. 4 (Apr. 1991), pp. 440–444.

Bachet, J., M. D., Gigou, F., M. D., Laurian, C., M. D., Bical, O., M. D., Goudot, B., M. D., Guilmet, D, M. D.: "Four-year clinical experience with the gelatin-resorcine-formol biological glue in acute aortic dissection." *J. Thorac. Cardioavasc. Surg.* vol. 83 (1982), pp. 212–215.

Fabiani, Jean-Nöel, M. D., Jebara, Victor A., M. D., Deloche, Alain, M. D., Stephan, Yves, M. D., Carpentier, Alain, M.D., PhD.: "Use of Surgical Glue Without Replacement in the Treatment of Type A Aortic Dissection." *Supplement I Circulation* vol. 80, No. 3 (Sep. 1989), pp. I264–I268.

Fabiani, Jean-Nöel, M. D., Gebara, Victor A., M. D., DeLoche, Alain, M. D., Carpentier, Alain, M. D. PhD.: "Use of Glue Without Graft Replacement for Type A Dissections: A New Surgical Technique." *Ann. Thorac. Surg.* 143–145 (1990), pp. 143–145.

Bachet, J., M. D., Goudot, B., M. D., Teodori, G., M. D., Brodaty, D., M. D., Dubois, C., M. D., De Lentdecker, Ph., M. D., Guilmet, D, M. D.: "Surgery of type A acute aortic dissection with Gelatine-Resorcine-Formol biological glue: A twelve-year experience." *J. Cardiovasc. Surg.* vol. 31 pp. 263–273 (Aug. 1990).

Laitakari, Kyösti, M. D., Luotonen, Jukks, M. D.: "Autologous and Homologous Fibrinogen Sealants: Adhesive Strength." *Laryngoscope* vol. 99 (Sep. 1989), pp. 974–976.

Lyons, Michael B., M. D., Lyons, George D., M. D., Webster, Douglas, PhD, Wheeler, Valerie R. M. D.: "Adhesives in Larynx Repair", *Laryngoscope* vol. 99 (Apr. 1989), pp. 376–381.

Sindou, Marc, M. D., D.Sc. Biol., Gilg, Alain, M. D., Vighetto, Alain, M. D., and Jouvet, Ane, M. D.: "Cryptic Angioma in the Trochlear Nerve. Excision of the Invaded Portion and Successful Repair with an Autologous Graft: Case Report," *Neurosurgery* vol. 30, No. 2 (1992).

Mandel, Mar. A., M. D.: "Closure of Blepharoplasty Incisions With Autologous Fibrin Glue", *Arch Opthamol* vol. 108, (Jun. 1990) pp. 842–844.

Dubrow, Terry, M. D., Schwartz, Robert J., M. D., McKissock, John M. D., Wilson, Samuel E., M.D.: "Effect of Aerosolized Fibrin Solution on Intraperitoneal Contamination." *Arch. Surg.* vol. 126, (Jan. 1991), pp. 80–83.

Dresdale, Arthur, M. D., Rose, Eric A., M. D., Jeevanandam, Valluvan, M. D., Recemtama, Keigh, M. D., Bowman, Fredrick O., M. D., and Malm, James R., M. D.: "Preparation of Fibrin Glue From Single-Donor Fresh -Frozen Plasma." *Surgery* vol. 97, No. 6 (1985) pp. 750–754.

"Tissue glass and the fibrin glue system [Cze]." *Rozhldey V Chirugii* 70(5) (Mar. 1991), Abstract.

Cartwright, R. A., McKinney, P. A., O'Brien, C., Richards, I. D., Roberts, B. Lander, I., Darwin, C. M., Bernard, S. M., Bird, C. C.: "Non-Hodgkin's Lymphoma: Case Control Epidemiological Study in Yorkshire Institution." Abstract From the Department of Pathology, University of Leeds, U.K. Journal Lukemia Research 12(1):81–8, (1988), Abstract.

Harris, David M., PhD., Siedentop, Karl H., M. D., Sanchez, Ben, M. D.: "Analogous Fibrin Tissuew Adhesive Factors Influencing Bonding Power", Abstract from *Laryngoscope* vol. 98 (Jul. 1988), Abstract.

ADHESIVE COMPOSITION AND METHOD

This is a continuation of copending application(s) Ser. No. 07/908,474 filed on Jul. 6, 1992, now abandoned.

BACKGROUND OF THE INVENTION

1. Field of the Invention

This invention relates to adhesive compositions generally, and more particularly to tissue adhesives useful in the practice of medicine and surgery on human or animal subjects. In general, the adhesive is of high strength, stronger than sutures for example, and creates a non-toxic bond in 30 seconds or less. It works well under wet conditions.

The adhesive compositions are based on cross-linked proteinaceous material of human or animal origin. The compositions provide strong and rapid bonding to a wide range of substrates of natural or synthetic origin, providing a broad range of possible applications. Thus the compositions of present invention bond to living tissues, including muscle, skin, connective tissue, nerve tissue, vascular and cardiac tissues, adipose tissue, cartilage, bone, and the like, as well as to corresponding cadaver tissues, which may be preserved or otherwise chemically treated. Strong bonds are also formed to natural or synthetic materials such as leather, rubber, Dacron, Teflon, and the like, as well as to metals, enabling the use of these compositions for the attachment of surgical grafts and devices, as well as for wound closure, trauma repair, hemostasis, and the like in the practice of human or veterinary medicine. Non medical applications of the adhesive are also anticipated.

In addition to compositions, the invention further relates to the methods of generating the adhesive compositions, and to the methods of achieving bonding or hemostasis through the generation of these compositions in situ.

2. Description of the Related Art

Various types of tissue adhesives are already known in the art. Three of these, namely the cyanoacrylates, gelatin-formaldehyde compositions, and fibrin based glues, have received most attention. For example, fibrin (a blood-clotting protein) and gelatin formaldehyde have each been utilized in surgical adhesive applications as have cyanoacrylates. Such adhesives work to a limited degree but have drawbacks as indicated below.

Several cyanoacrylates have been investigated for surgical use. For instance, some isobutyl cyanoacrylate formulations have been approved for veterinary use. Typically, monomer or a mixture of oligomers and/or monomer is applied to the site to be bonded where it rapidly polymerizes forming an adherent solid. One disadvantage of cyanoacrylate glues is that they require a dry field. Another is that the solid produced is non-absorbable, which limits the usefulness of the glue in internal applications. Also, the polymerization tends to be quite exothermic and adverse tissue response has been reported. There are a number of citations relating to this type of prior art indicated in the references listed at the end of this specification.

Glues based on gelatins cross linked with formaldehyde have been used experimentally, principally in Europe, since about 1964. Several formulations have been proposed of which "GRF" (gelatin, resorcinol, formol) is best known. Hot solutions of select gelatin are mixed in situ with a curing agent consisting primarily of formaldehyde solution. The mixture rapidly sets to a solid which adheres to tissues. The chief objection to GRF glues has been the obligatory use of formaldehyde, a known hazardous material. Also, the gelatin must be applied hot, significantly above body temperature, and the techniques of mixing and application are quite critical for successful use of GRF. Pertinent references relating to GRF glues are listed in the References section.

Fibrin Glues utilize the natural processes of blood clot formation to generate an adhesive or sealant composition. One commercial product is "Tussicol" ®, Rugis, France. Another is "Fibrin Sealant Kit 1.0" available from Osterreiehisehes Institut fur Ilaemoderivate, GMBH, subsidiary of Immuno AG, A-1220, Vienna, Austria. Two components are combined to form an artificial blood clot. One of the components is a solution of fibrinogen and blood clotting factors such as Factor XIII, and the other is primarily a solution of thrombin and calcium ion. Disadvantages of fibrin glues include their very low strength (generally less than 50 g./sq. cm.) and relatively slow set up time. Also, the use of blood products (fibrinogen and co-factors) from multiple human donors presents an inherent risk of transmitting certain diseases to the patient. Procedures have been proposed for using autologous blood to prepare fibrin sealant. See for instance Reference 20 in the References section.

SUMMARY OF THE INVENTION

As a surgical adhesive, the compositions of the invention have a bonding strength that is many times stronger than conventional fibrin adhesives and traditional sutures. For instance, several experimental surgical procedures were successfully carried out (in a porcine model) using the adhesive composition. For example, a perforated aorta and bowel were repaired by gluing patch materials to the lesions, and hemostasis was quickly achieved in a resected spleen by application of the adhesive.

The adhesive compositions of the present invention are the products of cross-linking on a surface or surfaces to be bonded of a mixture initially containing:

- Part A.- a water soluble proteinaceous material of about 27–53% by weight of the mixture.
- Part B.- di- or polyaldehydes present in a weight ratio of one part by weight to every 20–60 parts of protein present by weight in the mixture and water, optionally containing non essential ingredients to make up the balance of the composition. The final cross-linked bonding compositions are water insoluble, rubbery or leathery proteinaceous solids substantially free of aldehydes, and adherent to the substrate to be bonded with a tear strength of at least 75 g./sq. cm.

Bonding is achieved by combining the two part system (the parts being referred herein as Part A and B, respectively), and allowing the mixture to react on the surface or surfaces to be bonded. Bond formation is rapid, generally requiting less than one minute to complete. The resulting adhesion is strong, generally providing bonds with tear strengths of 400–600 g./sq.cm. Tear strengths of 1300 g./sq.cm. have been obtained by using this invention. The upper limits of tear strength have not been determined, and they are not intended to be interpreted as limiting the invention.

Part A is an aqueous solution containing about 30–55% by weight of purified or mixed protein material. The balance is water, dilute buffer, and/or saline solution, optionally containing non-essential materials which do not significantly interfere with the adhesive forming reaction. Examples of such non-essential materials are neutral salts, carbohydrates, fibers and miscellaneous biological materials, wetting agents, antibiotics, preservatives, dyes, thickening agents, and the like. For example, nonessentials such as fibrinogen or poly(ethylene glycol) as shown in Examples 5 and 19 and in 9 respectively, hereof may be included.

Part B is a solution of a di- or polyaldehyde in water or other suitable medium. Glutaraldehyde in 5–15% solution is preferred, but other aldehyde materials are also suitable. Thus, aqueous glyoxal is satisfactory for Part B, as are aqueous mixtures of di- and polyaldehydes obtained by oxidative cleavage of carbohydrates and their derivatives with periodate, ozone, or the like. Other water soluble di- and/or polyaldehydes will be readily recognized as useful for the purpose of this invention.

When a mixture of Parts A and B is allowed to react on a surface or surfaces to be bonded, an adherent composition forms, generally in less than one minute, even 30 seconds or less. A wide range of substrates can be bonded by this process, as previously indicated. No significant exotherm is observed, and good adhesion is obtained to wet surfaces, thus providing a wide range of usefulness for the invention.

As previously stated, it is the composition of the mixture of Parts A and B prior to cure, and most particularly its protein content by weight, which describes the limits of useful bonding compositions. The manner in which the bonding composition is assembled in practice (prior to cure) is not a limiting factor, and may vary with the intended use. Preferred ranges of concentrations for Parts A and B which on mixing produce the bonding composition will be discussed below as well as in the Examples.

DESCRIPTION OF THE PREFERRED EMBODIMENTS

As already indicated, Part A of the adhesive composition is substantially an aqueous solution of a proteinaceous material of human or animal origin. Albumins including ovalbumins are preferred proteins, and serum albumins of human or animal origin are particularly preferred. The proteinaceous material may be a purified protein or a mixture in which the proteins such as serum albumins are the predominant ingredients. For example, the solid mixtures obtained by dehydration of blood plasma or serum, or of commercial solutions of stabilized plasma proteins, can be used to prepare Part A. These mixtures, generally referred to as plasma solids or serum solids, are known to contain albumins as their major ingredients, of the order of 50–90%. As used herein, the term "plasma" refers to whole blood from which the corpuscles have been removed by centrifugation. The term "serum" refers to plasma which has additionally been treated to prevent agglutination by removal of its fibrinogen and/or fibrin, or by inhibiting the fibrin clot formation through addition of reagents such as citrate or EDTA.

Part B of the adhesive composition is substantially an aqueous solution of di- or polyaldehydes. A wide range of these substances exist, and their usefulness is restricted largely by availability and by their solubility in water. For example, aqueous glyoxal (ethandial) is useful, as is aqueous glutaraldehyde (pentandial). Water soluble mixtures of di- and polyaldehydes prepared by oxidative cleavage of appropriate carbohydrates with periodate, ozone, or the like are also useful. Glutaraldehyde is the preferred dialdehyde ingredient of Part B.

When Parts A and B are brought together as described in the Examples hereinbelow, the resultant product rapidly hardens to a strong leathery or rubbery material within a short time of mixing, generally on the order of 15–30 seconds. Strong adhesion results if the adhesive composition is on one or both surfaces to be bonded and the surfaces are brought together before the bond hardens. Full bond strength is generally attained in less than a minute but those familiar with this art will recognize that manipulating variables such as the particular ingredients used as Parts A and B, temperature, and so forth will affect the rate of bond formation. For instance, markedly reduced cure rates are observed when di- or polyaldehydes derived by oxidative cleavage of carbohydrates are used as Part B. Likewise, when Part A is based on plasma solids, full bond strength is generally obtained about twice as fast as when purified bovine serum albumin is used.

As indicated previously, effective bonding results whenever the composite mixture of Parts A and B falls within the acceptable range specified above, that is, 27–53% by weight of protein, as well as the prerequisite amounts of dialdehyde and water, However, if said mixture is to be produced by mechanically mixing Parts A and B on the surface(s) to be bonded, there are some preferred ranges of concentration within which Parts A and B should fall to facilitate said mixing. Thus, it is preferred to utilize protein solutions (Part A) with a solids content of about 30–50% by weight, and to mix these with dialdehyde solutions (Part B) of 5–15% by weight.

When generating the adhesive compositions of this invention, the Parts A and B can be pre-mixed and applied to the surface(s) to be bonded immediately following mixing by means of a syringe, catheter or other device. Alternately, the Parts A and B can be applied simultaneously, as for example from a dual nozzle device and mixed on the surface(s) to be bonded. Sequential application of Parts A and B to the surfaces is also satisfactory with the sequence B, then A, then B preferred.

In practice it is most convenient to mix Part A (containing 40–47% proteins in solution A, the balance being water and non-essentials) with Part B (containing 5–15% of glutaraldehyde or other di- or polyaldehyde, the balance again being water and/or non-essentials). However, in some applications it may be preferable to deviate from the above concentrations of A and B, provided, however, that the composition of the resulting mixture remains within the limits specified earlier. It is also convenient in some applications to utilize a slight excess of B, since unreacted material is readily neutralized after the bond is formed. Dilute solutions of proteins, peptides, or amino acids applied at about 5% concentration are suitable for that purpose.

Most preferably, Part A is pasty and Part B is liquid. When combined a honey-like composition (looks and consistency) is obtained.

Part A may be prepared by dissolving in water the dry proteinaceous solids, optionally containing non essential materials, or the protein solids may be dissolved in water which may optionally contain said nonessentials. The dry proteinaceous solids may be prepared by lyophilization of dilute proteinaceous solutions such as plasma or serum, or of commercial plasma extenders such as Plasma-Plex® or Plasmanate®, which are stabilized, reconstituted solutions of plasma proteins containing about 5% protein by weight, or of other appropriate solutions. Purified protein powders such as human or animal serum albumins, ovalbumin, or mixtures of protein powders may also serve to prepare Part A.

Plasma-Plex® (Plasma-Plex Plasma protein fraction (human) USP 5% solution, heat treated, Armour Pharmaceutical Company, Kankakee, Ill., 60901) and Plasmanate® (Plasma protein fraction (human) USP 5% solution Miles, Inc. Cutter Biological, Elkhart, Ind., 46515, USA, Miles Canada, Inc., Etobiocoke, Ontario Canada) were used as described above.

An alternative route to the preparation of Part A is the concentration of dilute proteinaceous solutions to the required solids content. This approach is particularly useful for the preparation of adhesive from a patient's own blood or from screened blood obtained from a single donor. Many techniques are available for concentrating protein solutions and they are well known by those skilled in the art. Among them may be listed lyophilization and reconstitution (mentioned above), evaporation, contact with hygroscopic solids, dialysis, ultrafiltration, and vacuum centrifugal evaporation. Other methods of concentrating dilute solutions may be preferable in particular applications.

The proteinaceous ingredient of Part A may be a purified protein or a mixture of proteins. Albumins are generally preferred, and serum albumins of human or animal origin are particularly useful. For example, the gross mixture of materials obtained by lyophilizing plasma or serum and containing about 90% by weight of serum albumin is satisfactory for preparing Part A, as are purified human or bovine serum albumins. A mixture of bovine serum albumin (ca. 95 parts) and bovine fibrinogen (ca. 5 parts) is particularly useful, and results in very strong bonds, typically 800–1200 g/sq. cm. The solid mixture obtained by lyophilizing egg whites and consisting largely of ovalbumin, is also satisfactory for preparing Part A. Other sources of proteinaceous material will be apparent to practitioners of the art.

Preferred embodiments of the invention are further illustrated by the following Examples:

EXAMPLE 1

Dry plasma solids were obtained by lyophilizing fresh frozen human plasma. Water was added to this solid to produce a viscous solution containing 45% of solids by weight. This solutions was used as Part A. Part B was aqueous glutaraldehyde solution containing 10% of glutaraldehyde by weight. Two rectangular blocks of meat were sprayed lightly with B on the surfaces to be bonded. The surfaces were then coated with A to a thickness of 1–2 mm, and again sprayed with B. The ratio of A to B was 7 to 1 by weight. The surfaces were joined within about 10 seconds of the application of A and held in position until cure was complete, generally 15–60 seconds, depending on temperature and on the effectiveness of mixing A and B.

To determine tear strength the glued rectangular block of meat was attached with clamps to a spring balance at one end and to a variable weight on the other. The weight was increased progressively until the bond or adjoining meat broke. Tear strength was recorded in g./sq.cm. required to break the bond. Tear strengths were determined one minute after joining the surfaces, unless otherwise noted. Typical tear strengths for the above composition were 445 g./sq. cm.

When the sequence of application of A and B is reversed or when A and B are applied simultaneously or when A and B are pre-mixed immediately prior to application, essentially the same bond strengths are observed.

EXAMPLE 2

Same as Example 1, except that a heat treated 5% plasma protein fraction (human) USP was used to produce the dry solids, and its concentration within Part A was 47% by weight. Adhesion was achieved as described above. Tear strengths ranged from 550–624 g./sq. cm.

EXAMPLE 3

Bovine serum albumin was dissolved in water to produce a solution containing 40% by weight solids, which was then used as Part A as described in Example 1 to bond meat blocks. Tear strengths ranged from 514–629 b./sq. cm.

EXAMPLE 4

Human serum albumin solutions containing 40–45% by weight of protein were prepared by concentrating 25% solutions by means of dialysis. When these solutions were used as Part A in bonding as described above, the tear strengths ranged from 605–922 g./sq. cm.

EXAMPLE 5

When Part A was a solution with a solids content of 45.5% by weight and consisting of a mixture of bovine serum albumin and bovine fibrinogen in which the albumin constituted 90–97%, the resulting bond tear strengths ranged from 786 to over 1280 g./sq. cm.

EXAMPLE 6

Synthetic vascular prostheses made of Dacron and prostheses made of Teflon, as well as cadaver derived human vascular graft materials were successfully bonded to meat or to each other using any of the compositions described in all of the Examples included herein. For instance, the tear strength obtained with the composition of Example 5 for the bond between beef and woven Dacron vascular prosthesis was above 890 g./sq.cm. measured in shear mode while that to a Teflon graft was 670 g./sq.cm. Similarly, implantable medical electrodes coated with silicone rubber showed a tear strength of 1080 g./sq.cm. utilizing bovine serum albumin in Part A.

EXAMPLE 7

Part A, containing 30–32% by weight of human serum albumin was prepared from either fresh plasma or from stabilized 5% plasma protein solutions by ultrafiltration (both were done). When 50% aqueous glutaraldehyde was used as component B the tear strengths of the resulting bonds ranged between 267–335 g./sq.cm.

EXAMPLE 8

Part A was 30% by weight of human plasma protein prepared from 5% stabilized solution (USP) as described in Example 7 above. Part B was 25% by weight aqueous glutaraldehyde. Parts A and B were mixed in a weight ratio of 10 Parts A to 1 Part of B resulting in a mixture containing 27% proteins by weight. This mixture was immediately applied to the surfaces of two meat blocks and the blocks were joined. The resulting bond had a tear strength of 75 g./sq/cm/

EXAMPLE 9

When meat blocks were joined as described in Example 1, but using 47% aqueous bovine serum albumin as A and 10% aqueous glyoxal as B the tear strength was 333 g./sq.cm.

EXAMPLE 10

A specimen containing a high proportion of skin and adipose tissue was joined using as Part A an aqueous solution containing about 41% bovine serum albumin and 4% poly(thylene glycol) of 15–20000 molecular weight, and 10% glutaraldehyde as Part B. The tear strength of the bond produced was 1300 g./sq. cm.

EXAMPLE 11

The adhesive composition described in Example 1 was successfully used in several surgical procedures on a 35–40 lb. pig. The procedures carried out were applications of patches (without sutures) to perforated abdominal aorta and bowel, and hemostasis of resected spleen. The patches were cut from human cadaver pulmonary artery tissue processed for use as a graft material in human cardiovascular surgery.

EXAMPLE 12

Part A was 47% bovine serum albumin. Part B was prepared as follows: methyl glucoside (0.5 g.) was dissolved in water (4.1 mL) and oxidized with sodium periodate (1.0 g.) in the presence of sodium bicarbonate in an ice bath during 45 min. The products of this reaction are known to be a complex dialdehyde in about 10% concentration by weight, as well as non essential salts. This solution was used as Part B without purification. The mixture cured to a flexible bond in about one hour with a tear strength of 320 g./sq.cm.

EXAMPLE 13

Same as

EXAMPLE 11, but using trehalose (0.5 g.), sodium periodate (1.2 g.) and sodium bicarbonate (0.5 g.) as reagents dissolved in water (4.0 mL) in an ice bath to produce Part B. This product is known to contain a mixture of complex di-, tetra- and polymeric aldehydes in about 10% solution, along with non essential salts. Tear strength after one hour was 245 g./sq.cm.

EXAMPLE 14

As in Example 11, but using sucrose (0.5 g.), sodium periodate (1.0 g.), sodium bicarbonate (1.0 g.) and water (5.0 mL). The resulting product solution is known to contain a mixture of complete di-, tetra- and polyaldehydes in about 8%. Resulting bond strength was 364 g./sq. cm.

EXAMPLE 15

The solid mixture obtained by lyophilizing egg white, and consisting predominantly of ovalbumin, was dissolved in water to make solutions with a solids content ranging from 40–44.8%. When these solutions were used as Part A in adhesion studies using 10% aqueous glutaraldehyde as Part B, the tear strengths obtained ranged form 255–339 g./sq. cm.

EXAMPLE 16

Bovine serum albumin (BSA) was dissolved in water in the concentrations shown and used as Part A. Part B was 10% aqueous glutaraldehyde. The following tear strengths were measured:

| Weight % BSA | Tear Strength (gm/cm$^2$) |
| --- | --- |
| 25 | <50 |
| 30 | <50 |
| 35 | 100 |
| 40 | 514–629 |
| 45 | 610 |
| 50 | 96–557* |

*Too viscous to spread evenly.

EXAMPLE 17

Plasma-Plex ®, a 5% solution of human protein fraction (USP) was lyophilized, the resulting solids constituted with water to the concentrations shown below, and the solutions used as Part A. Part B was 10% aqueous glutaraldehyde. The following tear strengths were observed:

| Weight % HSA | Tear Strength (gm/cm$^2$) |
| --- | --- |
| 35 | <50 |
| 37 | 163–257 |
| 41 | 250–381 |
| 43 | 358–413 |
| 45 | 423–567+ |
| 47 | 550–624 |
| 51 | 400–527+ |
| 53 | 338–500 |
| 55 | 85–390* |

+Indicates that the substrate tissue tore rather than the bond.
*Too viscous to apply evenly.

EXAMPLE 18

As in Example 17, but using solids obtained by lyophilizing fresh frozen plasma gave the following tear strengths:

| Weight % HSA | Tear Strength (gm/cm$^2$) |
| --- | --- |
| 30 | 136–269 |
| 35 | 486 |
| 40 | 550+ |
| 45 | 444–445+ |
| 50 | 278–361 |
| 55 | 150–226* |
| 60 | -Not soluble- |

+Indicates substrate tissue tore rather than the bond.
*Too viscous to spread well.

EXAMPLE 19

Mixtures of proteins can be used in the concentration ranges of the invention for Part A. For example, bovine serum albumin (BSA) and bovine fibrinogen (BF) produce an excellent adhesive: Total solids (mixed) 45.5 weight percent.

| PERCENT BSA | PERCENT BF | Tear Strength (gm/cm$^2$) |
| --- | --- | --- |
| 97 | 3 | 708–1280+ |
| 93.3 | 6.7 | 797+ |
| 90 | 10 | 786 |

-continued

| PERCENT BSA | PERCENT BF | Tear Strength (gm/cm$^2$) |
|---|---|---|
| 80 | 20 | 736–237* |

+Indicates substrate tissue tore rather than the bond.
*BF not fully soluble, solution is rubbery.

Mixtures such as these i.e., 93 parts BSA to 7 parts BF@45–46% solids particularly bonded aggressively to Dacron and PTFE at strengths of 890+ to 1200+.

Generally, good bonding is achieved either by applying A or B first or simultaneously e.g., from a dual nozzle. Also, methods of mixing in situ provide good bonds. Parts A and B may be applied in sequence, B then A, then B; or A, then B; or simultaneously with mixing on the surface(s) to be bonded; or through a catheter or catheters; or via syringe or similar device immediately following pre-mixing.

REFERENCES

1. Dresdale, Arthur, M.D., Rose, Erie A., M.D., Jeevanandam, Valluvan, M.D., Reemtama, Keigh, M.D., Bowman, Frederick O., M.D., and Maim, James R., M.D.: "Preparation of Fibrin Glue From Single-Donor Fresh-Frozen Plasma." *Surgery* Vol. 97, No. 6 (1985).
2. Sindou, Marc, M.D., D. Sc. Biol., Gilg, Alain, M.D., Vighetto, Alain, M.D., and Jouvet, Anne, M.D.: "Cryptic Angioma in the Trochlear Nerve. Excision of the Invaded Portion and Successful Repair with an Autologous Graft: Case Report." *Neurosurgery* Vol. 30, No. 2 (1992).
3. Dubrow, Terry, M.D., Schwartz, Robert J., M.D., McKissock, John M.D., Wilson, Samuel E., M.D.: "Effect of Aerosolized Fibrin Solution on Intraperitoneal Contamination. *Arch. Surg.* Vol. 126, (January 1991).
4. Mandel, Mark A., M.D.: "Closure of Blepharoplasty Incisions With Autologous Fibrin Glue". *Arch Opthalmol* Vol. 108, (June 1990).
5. Lyons, Michael B., M.D., Lyons, George D., M.D., Webster, Douglas, PhD, Wheeler, Valerie R., M.D.: "Adhesives in Larynx Repair". *Laryngoscope* Vol. 99 (April 1989).
6. Laitakari, Kyösti, M.D., Luotonen, Jukka, M.D.: "Autologous and Homologous Fibrinogen Sealants: Adhesive Strength." *Laryngoscope* Vol. 99 (September 1989).
7. Bachet, J., M.D., Goudot, B., M.D., Teodori, G., M.D., Brodaty, D., M.D., Dubois, C., M.D., De Lentdecker, Ph., M.D., Guilmet, D., M.D.: "Surgery of type A acute aortic dissection with Gelatine-Resorcine-Formol biological glue: A twelve-year experience." *J. Cardiovasc. Surg.* Vol. 31 (1990).
8. Fabiani, Jean-Nöel, M.D., Gebara, Victor A., M.D., DeLoche, Alain, M.D., Carpentier, Alain, M.D. PhD.: "Use of Glue Without Graft Replacement for Type A Dissections: A New Surgical Technique." *Ann. Thorac. Surg.* 143–5 (1990).
9. Fabiani, Jean-Nöel, M.D., Jebara, Victor A., M.D., Deloche, Alain, M.D., Stephan, Yves, M.D., Carpentier, Alain, M.D., PhD.: "Use of Surgical Glue Without Replacement in the Treatment of Type A Aortic Dissection." *Supplement I Circulation* Vol. 80, No. 3 (September 1989).
10. Bachet, J., M.D., Gigou, F., M.D., Laurian, C., M.D., Bical, O., M.D., Goudot, B., M.D., Guilmet, D., M.D.: "Four-year clinical experience with the gelatin-resorcine-formol biological glue in acute aortic dissection." *J. Thorac. Cardiovasc. Surg.* Vol. 83 (1982).
11. Braunwald, Nina S., M.D., Gay, William, M.D., Tatooles, Constantine J., M.D.: "Evaluation of cross-linked gelatin as a tissue adhesive and hemostatic agent: An experimental study." *Surgery* Vol. 59, No. 6 (June 1966).
12. Marescaux, J. F., Aparahamian, M., Mutter, D., Loza, E., Wilhelm, M., Sonzini, P., Damge, C.: "Prevention of anastomosis leakage: an artificial connective tissue." *Br. J. Surg.* Vol. 78, No. 4 (April 1991).
13. Celik, H., Caner, H., Tahta, K., Özcan, O. E., Erbenti, A., Onol, B.: "Nonsuture closure of arterial defect by vein graft using isobutyl-2-cyanoacrylate as a tissue adhesive." *Journal of Neurosurgical Sciences* Vol. 35, No. 2 (April–June 1991).
14. Aprahamian, Marc, Lambert, Alain, Balboni, Ginette, Lefebvre, Francoise, Schmitthaeusler, Roland, Damge, Cristiane, Rabaud, Michel: "A new reconstituted connective tissue matrix: Preparation, biochemical, structural and mechanical studies." *Journal of biomedical Materials Research Vol.* 21 (1987).
15. Meyer, G., Muster, D., Schmitt, D., Jung, P., Jaeger, J. H.: "Bone Bonding Through Bioadhesives: Present Status." *Biomat., Med. Der., Art. Org.* 7(1) (1979).
16. Nina S. Braunwald, William Gray, and Constantine J. Tatooles, *Surgery*. June 1966, 1024–1030. Relates to GRF glue.
17. J. Bachet et al., L Thorac, Cardiovasc. Surg. 83: 212–217 (1982). Relates to GRF glue.
18. J-N. Fabiani et al., *Ann. Thorac. Surg.* 50:143–145 (1990). Relates to GRF glue.
19. J. Bachet et al., *J. Cardiovasc. Surg.* 31:263–273 (1990). Relates to GRF glue.
20. Arch. Opthalmol. 108: 842–844, (1990).

ABSTRACTS

1. "Tissue glues and the fibrin glue system [Cze]." *Rozhledy V Chirugii* 70(5) (March 1991).
2. Cartwright, R. A., McKinney, P A., O'Brien, C., Richards, I D., Roberts, B., Lauder, I., Darwin, C M., Bernard, S M., Bird, CC.: "Non-Hodgkin's Lymphoma: Case Control Epidemiological Study in Yorkshire Institution." Abstract From the Department of Pathology, University of Leeds, U.K. *Journal Lukemia Research* 12(1):81–8, (1988).
3. Harris, David M., PhD., Siedentop, Karl H., M.D., Sanchez, Ben, M.D.: "Autologous Fibrin Tissue Adhesive: Factors Influencing Bonding Power". Abstract from *Laryngoscope* Vol. 98 (July 1988).
4. Havlicek, K., Vlcek, B., Stastny, 1.: "Hemostatic and adhesive properties of fibrin tissue glue in an experiment." *Rozhledy V Chirugii* 70(5) (March 1991).
5. Havlicek, K., Vlcek, B., Stastny, 1.: "Fibrin tissue glue, its preparation and methods of application." *Rozhledy V Chirugii* 70(5) (March 1991).
6. Byrne, D. J., Hardy, J., Wood, R. A., Mcintosh, R., Cuschiefi, A.: "Effect of fibrin glues on the mechanical properties of healing wounds." *British Journal of Surgery* 78(7) (July 1991).
7. Rudigoz, R. C., Chabert, P.: "Use of fibrin glue in gynecology-obstetrics [Fre]." *Revue Francaisc De Gynecologie Et D Obstetrique* 85(10) (October 1990).

8. Beltramello, A., Benati, A., Perini, S., Maschio, A.: "Interventional angiography in neuropediatfics." *Childs Nervous System* 5(2) (April 1989).
9. Laitakari, K., Luotonen, J.: "Autologous and homologous fibrinogen sealants: adhesive strength." *Laryngoscope* 99(9) (September 1989).
10. Herter, T.: "Is there a preference among fibrin glues for nerve anastomosis? [Ger]." *Hno.* 37(6) (June 1989).
11. Gigauri, V. S., Movchun, A. A., Got'e, S. V., Sheremet'eva, G. F., Shidkov, I. L.: "Use of fibrin glue in surgery of parenchymatous organs [Rus]." *Khirurgiia* (4) (April 1989).
12. Sackett, D. L.: "Simple and inexpensive preparation of dried polyacrylamide gels for densitometry and/or storage." *Analytical Biochemistry* 179(2) (June 1989).
13. "Dura mater healing after repair with aponeurotic plasty. Comparison of results between classical sutures and fibrin adhesive glue. Fibrin adhesive in frontobasal injuries. An experimental study [Frei." *Neuro-Chirurgie* 34(5) (1988).
14. Beloglazova, S. E.: "Cyanoacrylate glues and their use in gynecology [Rus]. *Akusherstvo I Ginekologiia-Moskva* (5) (May 1988).
15. Feldman, M. D., Sataloft, R. T., Ballas, S. K.: "Autologous fibrin tissue adhesive for cerebrospinal fluid leaks: A controlled study of neurotoxicity." *American Journal of Otology.* 9±4) (July 1988).
16. Jebara, V. A., Fabiani, J. N., Couetil, J. P., Acar, C., Dreyfus, G., Delouche, A., Carpentier, A.: "Exclusive use of surgical glue without graft replacement for type A aortic dissection: A new technique." *European Heart Journal* (1989)
17. Brothers, M. F., Kaurmann, J. C., Fox, A. J., Deveikis, J. P.: "n-Butyl 2-cyanoacrylate-substitute for IBCA in interventional neuroradiology: histopathologic and polymerization time studies." *Ajnr—American Journal of Neuroradiology* 10(4) (July-August 1989).

PATENTS

1. Rose, Eric, Dresdale, Arthur: "Fibrin Adhesive Prepared as a Concentrate from Single Donor Fresh Frozen Plasma." U.S. Pat. No. 4,627,879, Issued Dec. 9, 1986.
2. Takehisa Matsuda, Minoo, Hiree Iwata, Suita, Tetsuro Itoh, Shiga: "Surgical Adhesive." U.S. Pat. No. 4,740,534, Issued Apr. 26, 1988.
3. Ritter, Wolfgang: "Surgical Adhesive Systems for Hard Body Tissues." U.S. Pat. No. 4, 626,310, Issued Dec. 2, 1986.
4. Robinson, Joseph R.: "Bioadhesive Compositions and Methods of Treatment Therewith." U.S. Pat. No. 4,983,392, Issued Jan. 8, 1991.
5. Rose, Eric, Dresdale, Arthur: "Fibrin Adhesive Prepared as a Concentrate From a Single Donor Fresh Frozen Plasma." U.S. Pat. No. 4,627,879, Issued Dec. 9, 1986.
6. Iwatsuki, Makoto, Hayashi, Toshio: "Silk-Fibroin and Humane Fibrinogen Adhesive Composition." U.S. Pat. No. 4,818,291, Issued Apr. 4, 1989.
7. Reimann, Albert: "Method of Processing Blood." U.S. Pat. No. 2,241,868, Issued May 13, 1941.
8. Bering, Edgar A., Jr.: "Fibrin Foam." U.S. Pat. No. 2,492,458, Issued Dec. 27, 1949.
9. Cornwell, Earl D., Dobija, Stephen: "Method of Treating Proteins With Saturated Aliphatic Polyamines and Resulting Product." U.S. Pat. No. 2,597,228, Issued May 20, 1952.
10. Schwarz, Otto, Linnau, Yendra, Löblich, Franz, Seelich, Thomas: "Tissue Adhesive." U.S. Pat. No. 4,362,567, Issued Dec. 7, 1982.
11. Schwarz, Otto, Linnau, Yendra, Löblich, Franz, Seelich, Thomas: "Tissue Adhesive." U.S. Pat. No. 4,414,976, Issued Nov. 15, 1983.
12. Stroetmann, Michael: "Enriched Plasma Derivative for Advancement of Wound Closure and Healing." U.S. Pat. No. 4,427,650, Issued Jan. 24, 1984.
13. Stroetmann, Michael: "Enriched Plasma Derivative for Enhancement of Wound Closure and Coverage." U.S. Pat. No. 4,427,651, Jan. 24, 1984.
14. Fuhge, Peter, Heimburger, Norbert, Stöhr, Hans-Arnold, Burk, Wolfgang: "Readily Dissolvable Lyophilized Fibrinogen Formulation." U.S. Pat. No. 4,650,678, Issued Mar. 17, 1987. 15. Dixon, France T.: "Crosslinked Anisotropic Mammalian Diaphragm in Surgical Reconstruction." U.S. Pat. No. 4,813,958, Issued Mar. 21, 1989.
16. Seelich, Thomas: "Method of Inactivating Reproductive Filterable Pathogens in Fibrinogen and Factor XIII Compositions." U.S. Pat. No. 4,816,251, Issued Mar. 18, 1989.
17. Kotitschke, Ronald, Stemberger, Axel W., Stephan, Wolfgang: "Method of Preparing a Sterile Plasma-Protein Solution Containing Fibrinogen and Factor XIII." U.S. Pat. No. 5,099,003, Issued Mar. 24, 1992.
18. Grauert, Hugo: "Defibrillated Blood or Blood Serum Formula." German Pat. No. 251,126, Issued Sep. 17, 1912.
19. Kumpe, Grhardt, Wormsbacher, Wilfried, Heimburger, Norbert, Fuhge, Peter, Preis, Hans-Martin: "Human Fibrinogen Aq. Solns. Pasteurisation—in Presence of Added Calcium as well as Usual Stabilizers." German Pat. No. 32 30 849 Al, Issued Feb. 1989.
20. "Frozen Fibrinogen Prepn.—by Dissolving Dry Fibrinogen in Low Salt Content Buffer Soln., Contg. Mono:Saccharide, and Freezing Soln. Obtd." Japanese Pat. No. 57149-229, Issued Sep. 1982.
21. "Production of Sponge For Local Haemostasis—Includes Coagulation of Blood Plasma Pretreated With Amino-Benzoic Acid Using Calcium Chloride Soln." Soviet Union Pat. No. 741-878, Issued Jun. 1980.

While this invention may be embodied in many different forms, there are described in detail herein specific preferred embodiments of the invention. The present disclosure is an exemplification of the principles of the invention and is not intended to limit the invention to the particular embodiments illustrated.

This completes the description of the preferred and alternate embodiments of the invention. Those skilled in the art may recognize other equivalents to the specific embodiment described herein which equivalents are intended to be encompassed by the claims attached hereto.

What is claimed is:

1. An adhesive composition comprised of a mixture of human or animal-derived protein material in an amount of about 27–53% by weight and a di- or polyaldehyde in an amount of about 1 Part by weight for every 20–60 Parts of protein by weight, balance substantially water, wherein the protein is human serum albumin.

2. The composition of claim 1 wherein the aldehyde is glutaraldehyde.

3. The composition of claim 1 wherein the concentration of protein is about 40-47 weight %.

4. The composition of claim 1 wherein the concentration of protein is about 35 to 43% by weight.

5. An adhesive composition comprised of a mixture of human or animal-derived protein material in an amount of about 27-53% by weight and a di- or polyaldehyde in an amount of about 1 Part by weight for every 20-60 Parts of protein by weight, balance substantially water, wherein the protein is animal serum albumin and the aldehyde is glutaraldehyde.

6. The composition of claim 5 wherein the concentration of protein is about 40-47 weight %.

7. The composition of claim 5 wherein the concentration of protein is about 35 to 43% by weight.

8. An adhesive composition comprised of a mixture of human or animal-derived protein material in an amount of about 27-53% by weight and a di-or polyaldehyde in an amount of about 1 Part by weight for every 20-60 Parts of protein by weight, balance substantially water, wherein the protein is bovine serum albumin.

9. The composition of claim 8 wherein the aldehyde is glutaraldehyde.

10. The composition of claim 8 wherein the concentration of protein is about 40-47 weight %.

11. The composition of claim 8 wherein the concentration of protein is about 35 to 43% by weight.

12. An adhesive composition comprised of a mixture of human or animal-derived protein material in an amount of about 27-53% by weight and a di-or polyaldehyde in an amount of about 1 Part by weight for every 20-60 Parts of protein by weight, balance substantially water, wherein the protein is concentrated human blood serum.

13. The composition of claim 12 wherein the aldehyde is glutaraldehyde.

14. The composition of claim 12 wherein the concentration of protein is about 40-47 weight %.

15. The composition of claim 12 wherein the concentration of protein is about 35 to 43% by weight.

16. An adhesive composition comprised of a mixture of human or animal-derived protein material in an amount of about 27-53% by weight and a di- or polyaldehyde in an amount of about 1 Part by weight for every 20-60 Parts of protein by weight, balance substantially water, wherein the protein is ovalbumin.

17. The composition of claim 16 wherein the aldehyde is glutaraldehyde.

18. The composition of claim 16 wherein the concentration of protein is about 40-47 weight %.

19. The composition of claim 16 wherein the concentration of protein is about 35 to 43% by weight.

* * * * *